(12) United States Patent
Langan

(10) Patent No.: US 6,699,273 B2
(45) Date of Patent: Mar. 2, 2004

(54) SLEEVE WELDING COLLAR

(75) Inventor: Raymond Langan, Galway (IE)

(73) Assignee: SciMed Life Systems, Inc., Maple Grove, MN (US)

( * ) Notice: Subject to any disclaimer, the term of this patent is extended or adjusted under 35 U.S.C. 154(b) by 59 days.

(21) Appl. No.: 10/066,939

(22) Filed: Feb. 4, 2002

(65) Prior Publication Data

US 2003/0149399 A1 Aug. 7, 2003

(51) Int. Cl.[7] .................................................. A61F 2/06
(52) U.S. Cl. .................... 623/1.11; 604/96.01; 604/103
(58) Field of Search ............... 604/96.01, 103, 604/103.05, 104, 264, 523, 533; 623/1.11, 1.12; 606/192, 194

(56) References Cited

U.S. PATENT DOCUMENTS

| | | | |
|---|---|---|---|
| 4,503,569 A | 3/1985 | Dutter | 3/1.4 |
| 4,512,338 A | 4/1985 | Balko et al. | 128/1 |
| 4,732,152 A | 3/1988 | Wallsten | 128/343 |
| 4,733,665 A | 3/1988 | Palmaz | 128/343 |
| 4,848,343 A | 7/1989 | Wallsten et al. | 128/343 |
| 4,950,227 A | 8/1990 | Savin et al. | 604/8 |
| 5,019,090 A | 5/1991 | Pinchuk | 528/91 |
| 5,047,045 A | 9/1991 | Arney et al. | 606/194 |
| 5,108,416 A | 4/1992 | Ryan et al. | 606/194 |
| 5,156,594 A | 10/1992 | Keith | 604/96 |
| 5,234,456 A | 8/1993 | Silvestrini | 606/194 |
| 5,258,020 A | 11/1993 | Froix | 623/1 |
| 5,403,341 A | 4/1995 | Solar | 606/198 |
| 5,409,495 A * | 4/1995 | Osborn | 623/1.11 |
| 5,443,458 A | 8/1995 | Eury | 604/891.1 |
| 5,549,552 A | 8/1996 | Peters et al. | 604/96 |
| 5,897,537 A | 4/1999 | Berg et al. | 604/282 |
| 5,938,653 A | 8/1999 | Pepin | 604/527 |
| 6,565,595 B1 * | 5/2003 | DiCaprio et al. | 623/1.11 |

* cited by examiner

Primary Examiner—L. Thanh
Assistant Examiner—Cris L. Rodriguez
(74) Attorney, Agent, or Firm—Vidas, Arrett & Steinkraus, P.A.

(57) ABSTRACT

A catheter comprises a catheter shaft, at least one sleeve and at least one collar. At least a portion of the catheter shaft having a medical balloon mounted thereon. The medical balloon defines at least one waist which comprises a first waist portion and a second waist portion. The at least one sleeve has an upper surface and a lower surface. A first portion of the lower surface is engaged to the first waist portion. The at least one collar comprises a first collar portion and a second collar portion. The first collar portion is engaged to at least a portion of the upper surface of the at least one sleeve and the second collar portion is welded to the second waist portion of the medical balloon.

15 Claims, 4 Drawing Sheets

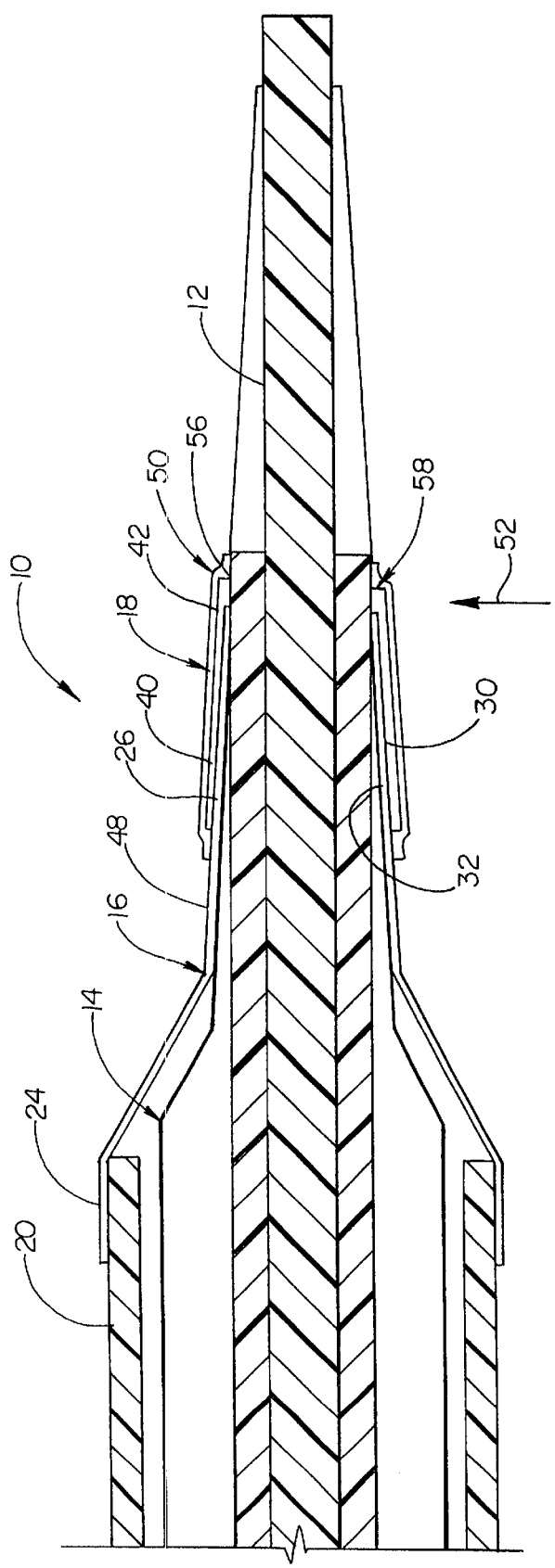

SLEEVE WELDING COLLAR

CROSS-REFERENCE TO RELATED APPLICATIONS

Not Applicable

STATEMENT REGARDING FEDERALLY SPONSORED RESEARCH

Not Applicable

BACKGROUND OF THE INVENTION

This invention relates to the field of intravascular medical devices, and more particularly to the field of catheters such as angioplasty, neurological and guide catheters, among others. Catheters may be used in various medical procedures such as percutaneous transluminal angioplasty (PTA), percutaneous transluminal coronary angioplasty (PTCA) as well as in procedures involving the placement of medicines and medical devices within the body. The present invention is directed to all forms of catheters which may be advanced through a body lumen or vessel. Some examples of catheters are over-the-wire (OTW) catheters, such as are described in U.S. Pat. No. 5,047,045; single-operator-exchange (SOE) balloon catheters, such as are described in U.S. Pat. No. 5,156,594 and U.S. Pat. No. 5,549,552. Other examples of catheters which may incorporate the unique features of the present invention are also described in U.S. Pat. Nos. 5,938,653, 5,897,537, among others.

Many procedures make use of a guide catheter positioned within the vascular system of a patient. The guiding catheter assists in transporting a balloon dilation catheter, or other form of treatment catheter, to the portion of the vessel requiring treatment or inspection. The guide catheter is urged through the vasculature of the patient until its distal end is proximate the restriction. The balloon catheter may then be fed through a lumen in the guide catheter.

Balloon catheters may be used to widen a vessel into which the catheter is inserted by dilating the blocked vessel, such as in an angioplasty procedure. Balloon catheters may also be used to expand and/or seat a medical device such as a stent, graft, stent-graft, vena cava filter or other implantable medical device at a desired position within a body lumen. In such applications, fluid under pressure is supplied to the balloon through an inflation lumen in the catheter, thereby expanding the balloon.

Intravascular diseases are commonly treated by relatively non-invasive techniques such as PTA and PTCA. These angioplasty techniques typically involve the use of a balloon catheter. In typical PTCA procedures, a guiding catheter is percutaneously introduced into the cardiovascular system of a patient through a vessel and advanced through therein until the distal end thereof is at a desired location in the vasculature. A guide wire and a dilatation catheter having a balloon on the distal end thereof are introduced through the guiding catheter with the guide wire sliding through the dilatation catheter. The guide wire is first advanced out of the guiding catheter into the patient's coronary vasculature and the dilatation catheter is advanced over the previously advanced guide wire until the dilatation balloon is properly positioned across the lesion. Once in position across the lesion, the flexible, expandable, preformed balloon is inflated to a predetermined size with a liquid or gas at relatively high pressures, to radially compress the arthrosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be injury to or restenosis of the artery, which either necessitates another angioplasty procedure, a surgical by-pass operation, or some method of repairing or strengthening the area. To strengthen the area and help prevent restenosis, a physician can implant an intravascular prosthesis for maintaining vascular patency, commonly called a stent, inside the artery at the lesion.

A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Stents are generally tubular in configuration, open ended and are expandable between a generally unexpanded insertion diameter and an expanded implantation diameter. Stents are commonly placed or implanted by a mechanical transluminal procedure.

Self-expanding, inflation expandable and hybrid stents are well known and widely available in a variety of designs and configurations. Self-expanding stents may be retained on a catheter shaft prior to delivery through the use of a sheath, sleeve(s), sock or other retaining member which function to maintain the stent is a reduced diameter configuration during advancement of the catheter to the stent deployment site. Inflation expandable and hybrid stents may be crimped to their reduced diameter about the delivery catheter, then maneuvered to the deployment site and expanded to the vessel diameter by fluid inflation of a balloon positioned between the stent and the delivery catheter. All types of stents however may be retained in a reduced profile configuration by the one or more sheathes, sleeves, sock or other retaining members.

Some examples of stents are described in the following U.S. patent references: U.S. Pat. Nos. 4,733,665; 5,019,090; 4,503,569; 4,512,338; 4,732,152; 4,848,343; 5,234,456; 5,443,458; and 5,258,020.

Stent delivery and deployment assemblies are known which utilize restraining means that overlie the stent during delivery. U.S. Pat. No. 4,950,227 to Savin et al., relates to an inflation expandable stent delivery system in which a sleeve overlaps the distal or proximal margin (or both) of the stent during delivery. During inflation of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site.

Some other examples of stent delivery assemblies are described in the following U.S. patent references: U.S. Pat. Nos. 5,571,135; 5,445,646; 5,571,168; 5,702,418; 5,733,267; 5,817,101; 5,893,868; 5,944,726; 5,989,280; 5,980,530; 5,980,533; 5,968,052; 5,968,069; 6,007,543; 6,042,588; 6,056,759; 6,059,813; 6,066,155; 6,068,634; 6,113,608; 6,120,522; 6,117,140; 6,139,524; 6,168,617; 6,206,888; 6,254,609; 6,221,097; 6,238,402; and 6,270,504.

In many catheters, particularly in many of those used in medical device delivery procedures, a catheter may be equipped with one or more members including but not limited to: sheaths, sleeves, socks, collars, bands an/or any other member, collectively and hereinafter referred to generically as "sleeves". In some cases, the sleeve(s), or a portion thereof, may be engaged or otherwise secured to a portion of the catheter shaft and/or portion of a balloon, in a variety of manners including, frictional engagement, adhesive engagement, chemical and/or thermal bonding or welding, etc.

However, many securement methods and configurations have difficulty properly securing a member to a catheter or balloon where the respective materials are incompatible. In addition, some sleeves, when secured to a catheter using prior a securement methods have a tensile strength which is less than desired. As a result, it would be desirable to provide a catheter assembly with a member engagement method and/or configuration particularly suited for bonding components such as sleeves and/or other types of members to the catheter shaft or balloon waist regardless of the material composition of the catheter, balloon and/or components. In addition it would be desirable to provide a securement method which results in a sleeve having a greater tensile strength than that which is provided by some prior methods.

All U.S. patents and applications and all other published documents mentioned anywhere in this application are incorporated herein by reference in their entirety.

The invention in various of its embodiment is summarized below. Additional details of the invention and/or additional embodiments of the invention may be found in the Detailed Description of the Invention below.

The abstract provided herewith is intended to comply with 37 CFR 1.72 and is not intended be used in determining the scope of the claimed invention.

BRIEF SUMMARY OF THE INVENTION

The present invention may be embodied in a variety of different forms. At least one embodiment of the invention is directed to a collar for use with a catheter. Preferably the collar is used with a balloon catheter having one or more components such as sleeves mounted thereon herein after collectively referred to as sleeves. The inventive collar is preferably constructed from the same material as the balloon. The collar is disposed about the sleeve where the sleeve overlaps the balloon waist. A heat source such as an annular laser, heats the collar and the underlying materials to a point where the collar material is fused or welded to the balloon waist. As a result, the portion of the sleeve overlapped by the collar and balloon waist may be encased within the now fused collar and balloon waist materials. In a preferred embodiment, the portion of the sleeve overlapped by both the collar and balloon waist is fused or welded to one or both of the collar and balloon material.

Details of these and other embodiments of the invention are discussed below.

BRIEF DESCRIPTION OF THE SEVERAL VIEWS OF THE DRAWINGS

A detailed description of the invention is hereafter described with specific reference being made to the drawings in which:

FIG. 4 is a partial side elevational view of an embodiment of the invention.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
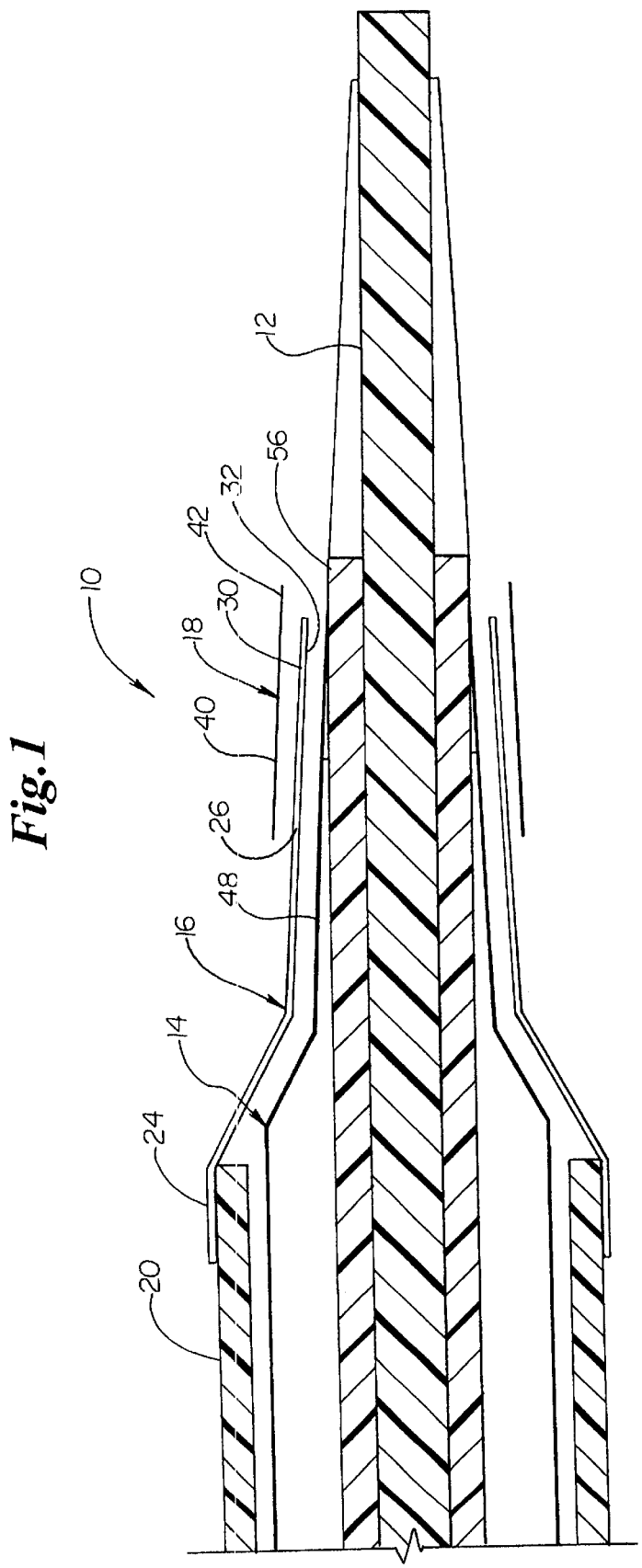
FIG. 1 is a partial side elevational view of an embodiment of the invention shown prior to welding.

As indicated above the present invention may be directed to several embodiments. In FIG. 1, an embodiment is shown wherein a portion of a catheter, indicated generally at 10, is shown in a process of assembly. In the embodiment shown, catheter 10 may include several components including: a catheter shaft 12 an inflatable portion or medical balloon 14, a sleeve 16 and a retaining collar 18. It should be noted that for purposes of descriptive clarity sleeve 16 and collar 18 are shown spaced apart.

Figure 3:
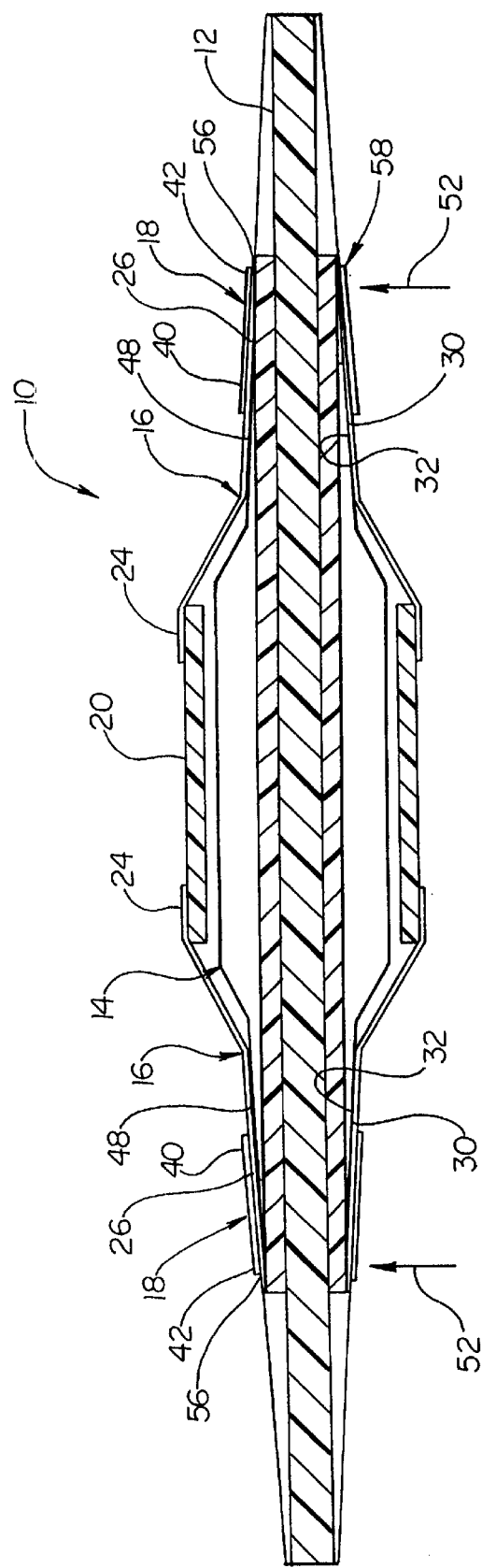
FIG. 3 is a side elevational view of an embodiment of the invention shown in FIG. 2.

In some embodiments, where catheter 10 is utilized for delivery of a medical device, a medical device such as a stent 20, may be disposed about at least a portion of the balloon 14. Where the catheter 10 includes a stent 20, the catheter preferably includes a first or proximal sleeve 16 disposed about the proximal end of the balloon 14 and a second or distal sleeve 16 disposed about the distal end of the balloon 14 as is shown in FIG. 3. However, in some embodiments a single sleeve 16 may be mounted either proximal or distal of the stent 20 to secure the stent in a reduced state about the catheter shaft 10. When affixed to the catheter shaft 12, sleeve 16 substantially overlaps the balloon waist 48.

In the present embodiment shown in FIG. 1, at least one sleeve 16 is positioned around the catheter 10. A first end portion 24 of the sleeve 16 overlaps a portion of the stent 20 and a second portion 26 overlaps a portion of the balloon 14, including waist portion 48.

Sleeve 16 may be elastomeric in nature so as to stretch and release the stent when it expands for implantation. The sleeve 16 may be constructed from one or more materials. Suitable sleeve material for use in constructing sleeve 16 may include but is not limited to: thermoplastic elastomers i.e. block copolymers; copolymers and terpolymers of ethylene; homopolymers, copolymers and terpolymers of propylene; ethylene α-olefins; polyesters; polyamides; polyurethanes, such as TECOTHANE™ a biocompatible medical grade aromic polyurethane available from Thermedics, Inc.; polycarbonates; polycarbonate-polyurethane co-polymer; polyurethane-polycarbonate blends; vinyl copolymers; ionomer materials and so forth. More specifically, materials such as nylon, SELAR™, polyether-polyester block copolymers (i.e. HYTREL™ from DuPont or ARNITEL™ from DSM, Netherlands), PEBAX™ (polyether block amide copolymers), SURLYN™, polyethylene terephthalate, polytetrafluoroethylene, polyvinyl chloride, polyetherurethanes, polyesterurethanes, polyurethane ureas, polyurethane siloxane block copolymers, silicone polycarbonate copolymers, ethylene vinyl acetate copolymers, acrylonitrile-butadiene-styrene copolymers; polyphenylene sulfides; copolyesters or other similar extrudable thermoplastic, polymeric materials, and/or composites thereof may be utilized in the present invention.

In some embodiments, the sleeve 16 is constructed from a specific polyurethane such as TECOTHANE™, a mixture of polycarbonate-polyurethane co-polymers such as CARBOTHANE™, CHRONOFLEX™ from CT Biomaterials or any combinations thereof.

The sleeve 16 may be characterized as including an upper surface 30 and a lower surface 32. When the catheter 10 is fully assembled such as is shown in FIGS. 2–4, preferably, at least a portion of the lower surface 32 is engaged to a portion of the balloon 14 and a portion of the upper surface 30 is engaged to at least a portion of the collar 18.

In the various embodiments shown in FIGS. 1–4, the collar 18 may be characterized as having two portions. A first portion 40 of the collar 18 overlies a portion of the sleeve 16 which itself overlies a portion of the balloon waist 48. A second portion 42 of the collar 18 overlies a portion of the balloon waist 48 directly.

Figure 2:
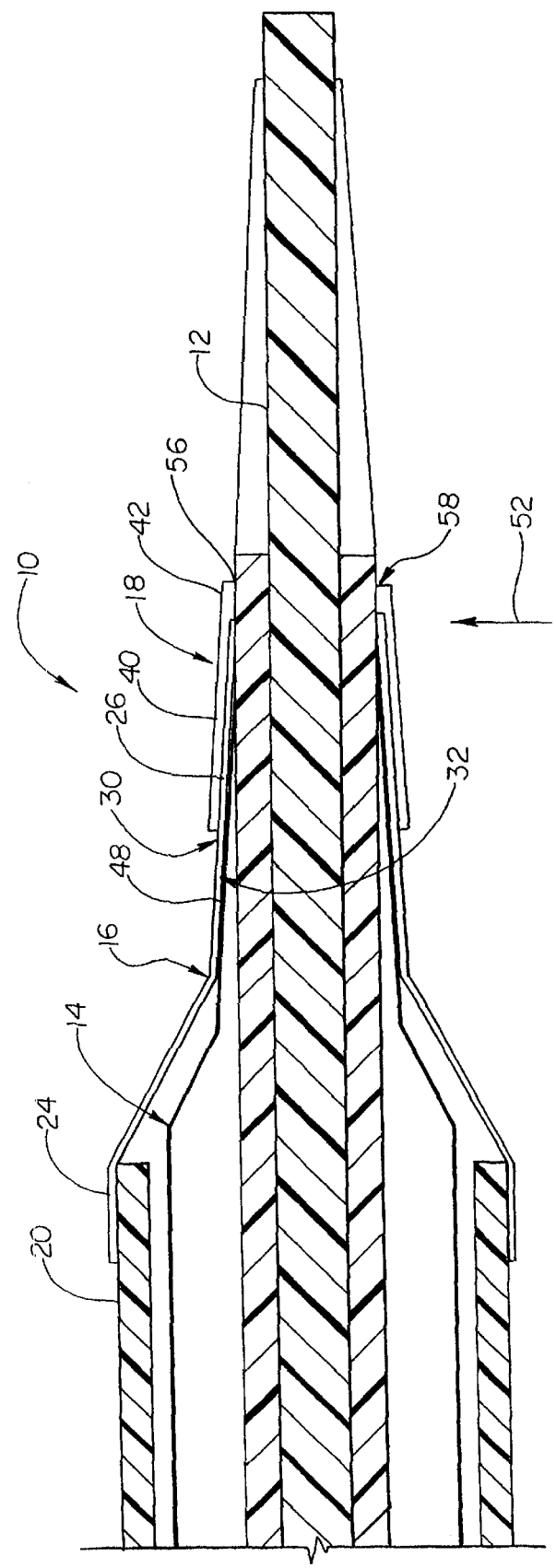
FIG. 2 is a partial side elevational view of an embodiment of the invention.

When catheter 10 is fully assembled such as may be seen in FIGS. 2 and 3, a portion of the upper surface 30 of the sleeve 16 is engaged to a portion of the collar 18, and a portion of the lower surface 32 is engaged to a portion of the balloon waist 48. Preferably, the collar 18 has a length which extends beyond the length of the sleeve 16 such that a portion of the collar 18 is in contact with the end of the balloon waist 48. In some embodiments the collar 18 may also be in contact with a portion of the catheter shaft 12 immediately adjacent to the balloon waist 48.

In at least one embodiment of the invention the collar 18 is about 2.0 mm in length. In some embodiments, the first portion 40 is preferably about 1.0 mm to about 1.5 mm in length. In some embodiments the second portion 42 is about 0.5 mm or more in length.

The collar 18 is preferably made from the same material that balloon 14 is constructed from. The balloon 14 and collar 18 maybe made of any suitable balloon material including Pebax™ 7233. Other suitable materials include, but are not limited to those described in U.S. Pat. Nos. 6,024,752, and 6,036,697 the entire contents of which are incorporated herein by reference.

In at least one embodiment of the invention the collar 18 is about 1.0 mm to about 2.0 mm long with an inner diameter of about 0.035 inches (about 0.8 mm to about 0.9 mm) and has a tensile strength of about 0.7 lbs. to about 1.2 lbs.

When the, various components are assembled in the manner shown in FIG. 1, a heat shrink layer 50 may be placed over the collar 18 to secure the collar 18 to the catheter such as is shown in FIG. 4. In an alternative embodiment, the collar 18 may be a heat shrink material. Heat shrink 50 may be any heat shrink material suitable for use in a medical device. Such heat shrink materials are well known. Some examples of materials that may be used include but are not limited to polytetrafluoroethylene (Teflon), polyethylene materials such as polyolefin, etc. An specific example of a suitable heat shrink material may be RNF-100 a heat shrink tubing available from Raychem Corporation.

When the collar 18 is held in place by the heat shrink 50 or some other securement means, such as by adhesive or frictional engagement, heat energy, represented by arrow 52, may be transmitted to the collar 18, such as is shown in FIGS. 2–4.

Many different heat sources may be utilized to provide energy 52. For example the material may be directly heated by a heating element. Indirect energy sources may include IR, UV, laser or other energy transmission devices.

Preferably energy 52 is provided by an Annular laser. The energy 52 supplied by the laser heats the collar 18 as well as at least a portion of the balloon 14 in contact therewith to a preferred weld temperature of about 220 degrees Celsius. The weld temperature may be any temperature suitable to cause collar 18 and balloon waist 48 to melt and thereby fuse together when cooled.

As a result of the application of energy 52, the end portion 42 of the collar 18 and an end portion 56 of the balloon waist 48 are bonded together by a circumferential weld 58, shown in FIGS. 2–4. Where the catheter 10 includes a heat shrink layer 50, such as is shown in FIG. 4, during the heating process the heat shrink 50 will force the end portion 42 of the collar 18 and an end portion 56 of the balloon waist 48 to ensure that the weld is complete.

In some embodiments, where sleeve 16 has a melting point equal to or less than the weld temperature, the material of portion 26 of sleeve 16 may also be melted together with the collar 18 and balloon waist 48 thereby forming a three component weld 58.

A consequence of welding end portion 42 of the collar 18 and end portion 56 of the balloon waist 48 together is that at least a portion of portion 26 of sleeve 16 will be encased within the combined material of the collar 18 and balloon waist 48. The encasement of the sleeve 16 between the collar 18 and balloon waist 48 provides the sleeve with significantly improved tensile strength than a sleeve laser welded to a catheter without a collar 18. In the embodiment shown in FIGS. 2–4, sleeve 16 has a tensile strength of about 0.8 lbs to about 1.7 lbs. In some embodiments, tensile strength of a sleeve 16 encased between collar 18 and balloon waist 48 has been measured at 0.92 lbs., 1.43 lbs. and 1.51 lbs. respectively.

Subsequent to welding the collar 18 and balloon waist 48 together, heat shrink 50 may be removed such as is shown in FIGS. 2 and 3. If the heat shrink is a biocompatible material, the heat shrink may be left in place as is shown in FIG. 4.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

What is claimed is:

1. A catheter comprising:
   a catheter shaft, at least a portion of the catheter shaft having a medical balloon mounted thereon, the medical balloon comprising a first waist portion and a second waist portion;
   an implantable medical device having a reduced state and an expanded state, in the reduced state the implantable medical device is disposed about a portion of the balloon adjacent to at least one waist, the implantable medical device being selected from the group consisting of: a stent, a graft, a stent-graft, a vena cava filter and any combination thereof;
   at least one sleeve, the at least one sleeve having an upper surface and a lower surface, a first portion of the lower surface being engaged to the first waist portion, when the implantable medical device is in the reduced state a second portion of the lower surface of the at least one sleeve overlappingly engages at least a portion of the implantable medical device; and
   at least one collar, the at least one collar comprising a first collar portion and a second collar portion, the first collar portion being engaged to at least a portion of the upper surface of the at least one sleeve, the second collar portion being welded to the second waist portion of the medical balloon.

2. The catheter of claim 1 wherein the at least one collar and the at least one waist are constructed from the same materials.

3. The catheter of claim 1 wherein the at least one collar and the at least one waist are constructed from materials which have similar melting points.

4. The catheter of claim 1 wherein the at least one collar, the at least one waist and the at least one sleeve are constructed from the same materials.

5. The catheter of claim 1 wherein the at least one collar, the at least one waist, and the at least one sleeve are constructed from materials which have similar melting points.

6. The catheter of claim 1 wherein the at least one sleeve is constructed from at least one material of the group consisting of: thermoplastic elastomers i.e. block copolymers; copolymers and terpolymers of ethylene; homopolymers, copolymers and terpolymers of propylene; ethylene α-olefins; polyesters; polyamides; polyurethanes; polycarbonates; polycarbonate-polyurethane co-polymer; polyurethane-polycarbonate blends; vinyl copolymers; nylon, polyether-polyester block copolymers, polyether block amide copolymers, polyethylene terephthalate, polytetrafluoroethylene, polyvinyl chloride, polyetherurethanes, polyesterurethanes, polyurethane ureas, polyurethane siloxane block copolymers, silicone polycarbonate copolymers, ethylene vinyl acetate copolymers, acrylonitrile-butadiene-styrene copolymers; polyphenylene sulfides; copolyesters; and any combination thereof.

7. The catheter of claim 1 further comprising a heat shrink material, the heat shrink material being disposed about at least the at least one collar.

8. The catheter of claim 1 further comprising a heat shrink material, the heat shrink material being removably disposed about at least the at least one collar.

9. The catheter of claim 1 wherein the at least one collar is at least partially constructed from a heat shrink material.

10. The catheter of claim 1 wherein the second collar portion is laser welded to the second waist portion of the medical balloon.

11. The catheter of claim 1 wherein the second collar portion is circumferentially laser welded to the second waist portion of the medical balloon.

12. The catheter of claim 1 wherein the at least one sleeve has a tensile strength of about 0.8 lbs to about 1.7 lbs.

13. The catheter of claim 1 wherein the at least one collar is about 1.0 mm to about 2.0 mm in length.

14. A catheter comprising:
    a catheter shaft, at least a portion of the catheter shaft having a medical balloon mounted thereon, the medical balloon comprising a first waist portion and a second waist portion;
    at least one sleeve, the at least one sleeve having an upper surface and a lower surface, a first portion of the lower surface being engaged to the first waist portion; and
    at least one collar, the at least one collar comprising a first collar portion and a second collar portion, the first collar portion being engaged to at least a portion of the upper surface of the at least one sleeve, the second collar portion being welded to the second waist portion of the medical balloon, the at least one collar and the balloon being constructed from at least one polyether based material; an implantable medical device having a reduced state and an expanded state, in the reduced state the implantable medical device is disposed about a portion of the balloon adjacent to at least one waist, the implantable medical device being selected from the group consisting of: a stent, a graft, a stent-graft, a vena cava filter and any combination thereof, wherein when the implantable medical device is in the reduced state a second portion of the lower surface of the at least one sleeve overlappingly engages at least a portion of the implantable medical device.

15. The catheter of claim 14 wherein the at least one polyether based material is polyether block amide copolymer.

* * * * *